United States Patent
Shepard et al.

(10) Patent No.: US 6,551,585 B1
(45) Date of Patent: Apr. 22, 2003

(54) USE OF TUMOR NECROSIS FACTOR AS AN ADJUVANT

(75) Inventors: H. Michael Shepard, San Francisco, CA (US); James E. Talmadge, Frederick, MD (US)

(73) Assignees: Genentech, Inc., South San Francisco, CA (US); National Institutes of Health, Rockville, MD (US); The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 08/453,852

(22) Filed: May 30, 1995

Related U.S. Application Data

(60) Continuation of application No. 08/180,392, filed on Jan. 12, 1994, now abandoned, which is a continuation of application No. 07/946,244, filed on Sep. 16, 1992, now abandoned, which is a continuation of application No. 07/558,937, filed on Jul. 27, 1990, now abandoned, which is a division of application No. 07/007,075, filed on Jan. 21, 1987, now Pat. No. 4,963,354.

(51) Int. Cl.[7] .......................... A61K 45/00; C07K 17/00
(52) U.S. Cl. ...................................... 424/85.1; 530/351
(58) Field of Search ...................... 514/2, 12; 424/85.1; 530/351

(56) References Cited

U.S. PATENT DOCUMENTS

| | | | | |
|---|---|---|---|---|
| 4,709,011 A | * | 11/1987 | Cohen et al. | 530/324 |
| 4,812,554 A | * | 3/1989 | Riggs et al. | 530/311 |
| 4,963,354 A | * | 10/1990 | Shepard et al. | 424/85.1 |

OTHER PUBLICATIONS

Bachwich et al 1986, Biochem Biophys Res Commun 136(1): 94–101.*
Beutler et al 1985 Science 229: 869–871.*
Kato et al 1985 Immunology 54: 317–324.*
Kornbluth et al 1986 J Immunol 137: 2585–2591.*
Mason et al 1985 Nature 318: 659–663.*
Staruch et al 1983 J Immunol 130(5): 2191–2194.*

* cited by examiner

*Primary Examiner*—Karen Cochrane Carlson
(74) *Attorney, Agent, or Firm*—Diane L. Marschang

(57) ABSTRACT

Tumor necrosis factors, alone or together with cytokines such as IL-1 or IFN-γ, are capable of serving as non-toxic vaccine adjuvants.

4 Claims, No Drawings

USE OF TUMOR NECROSIS FACTOR AS AN ADJUVANT

This is a continuation of application(s) Ser. No. 08/180,392 filed on Jan. 12, 1994, now abandoned which is a continuation application of Ser. No. 07/946,244 filed on Sep. 16, 1992, now abandoned, which is a continuation application of Ser. No. 07/558,937 filed on Jul. 27, 1990, now abandoned, which is a divisional application of Ser. No. 07/007,075 filed on Jan. 21, 1987, which issued as U.S. Pat. No. 4,963,354 on Oct. 16, 1990, which applications are incorporated herein by reference.

International Application filed on, which designated the U.S., and which application(s) is (are) incorporated herein by reference and to which application(s) priority is claimed under 35 USC §120.

This invention relates to substances used to enhance or induce an immune response to an antigen. In particular, it is directed to the use of substances normally found in the body for such purposes.

Immunization is a critical component of many industrial and therapeutic processes. The capability to raise high titer, high specificity antisera against a selected antigen is important in the manufacture of antibodies for in vitro and in vivo use and for ensuring successful vaccinations. Vaccination is becoming significant outside its well-known role in protecting against infectious diseases. For example, vaccination against self or syngeneic tumors is a developing technology[1], as is the use of vaccination to control physiological processes such as reproduction and growth by inducing autoimmune responses that antagonize or agonize biological effector molecules in vivo. In all of these new approaches it is important to induce a vigorous immune response to the target antigen, either humoral or cell mediated. This heretofore has been accomplished by administering an adjuvant in connection with the antigen, and in some cases by complexing the antigen with a carrier. Adjuvants and carriers are substances that in themselves share no immune epitopes with the target antigen but which stimulate the immune response to the target antigen. Freund's adjuvant, a mineral oil emulsion, commonly has been used for this purpose, as have a variety of toxic microbial substances such as mycobacterial extracts[59, 60]. Carriers often act as adjuvants as well, but are generally distinguished from adjuvants in that carriers comprise water insoluble macromolecular particulate structures which aggregate the antigen. Typical carriers include aluminum hydroxide, latex particles, bentonite and liposomes.

Many diverse materials have been demonstrated to possess adjuvant activity, and their mechanisms of action are nearly as varied, as is apparent from several reviews on the subject[61,62,63,64]. Adjuvant effects have been attributed to antigen aggregation, antigen depot formation, altered lymphocyte recirculation, stimulation of T lymphocytes, mitogenic effects on B lymphocytes, activation of phospholipase A, inhibition of prostaglandin synthesis, cell membrane alterations, localization of antigens in thymus-dependent areas of lymph nodes, modified antigen processing by macrophages, and stimulation of macrophage replication and activation[65]. It is clear that the biology of adjuvants is quite complex and that a number of hypotheses exist for the mode of action of immune adjuvants.

Monokines such as interleukin-1 have been implicated as mediators in adjuvant effects. The adjuvant effect of IL-1 has been attributed to its activity as a lymphocyte growth factor[65,66,47]. Certain synthetic adjuvants also are known to be able to induce interferon synthesis[65] and coadministration of antigen and γ-interferon to mice is known to potentiate immune response to the antigen[9].

Potentially undesirable effects of the heretofore available adjuvants and adjuvant formulations are well known. A list of side effects of adjuvants includes: (1) sensitization to tuberculin or any other antigen used in screening tests for infections; (2) presence in food animals of materials that cannot safely be ingested by humans; (3) inflammatory, granulomatous, necrotizing, or other unacceptable reactions at injection sites most notably as occurs with Freund's complete adjuvant; (4) pyrogenicity; (5) central nervous system effects and untoward behavioral effects; (6) impairment of growth; (7) arthritis; (8) increased vascular permeability and inflammatory reactions in the eye; (9) induction of undesired autoimmune responses and (10) immune suppression for adjuvant epitopes.

Whether the induction of autoimmune responses is undesirable depends upon the therapeutic objective. For example, the induction of autoimmune responses such as allergic encephalomyelitis in a small minority of subjects would be a very undesirable property of an adjuvant for human use. In contrast, the generation of an autoimmune response is frequently the objective in the veterinary field, e.g., suppressing fertility in animals by inducing autoantibodies against luteinizing hormone-releasing hormone, increasing fertility by vaccinating against endogenous inhibin, or increasing growth by eliciting autoantibodies against somatostatin, and is also desirable in inducing an immune response to host tumors.

Vaccination adjuvants are needed which are capable of use so as to be free of the undesirable side effects noted, above. Accordingly, it is an object of the invention herein to enhance the titer and duration of the mammalian immune response, both humoral and cellular, without toxic reactions. This and other objects of the invention will be apparent from the specification as a whole.

Monocytes and lymphocytes are known to produce the cytokines TNF-α[8] and TNF-β (previously called lymphotoxin)[2,3], respectively. Their complete primary structures have been determined and the cDNAs of both TNF-β[4] and TNF-α[5-7,10] have been cloned by recombinant DNA methods and expressed in $E.\ coli$.

In vivo and in vitro studies using the pure TNFs have shown that both TNF-α and TNF-β possess the unique ability to kill neoplastic tissue selectively, while sparing most normal cells. In addition to their antitumor activity, these proteins mediate a diverse array of biological responses in vitro. Although their true in vivo significance is still unknown, the biologic studies strongly suggest that TNF-α and TNF-β play an important role in immunomodulatory and inflammoatory responses.

TNF-α and TNF-β differ significantly in their physical and chemical properties. TNF-α is a 157 residue polypeptide with a molecular weight of 17,000[8] by SDS-PAGE. Under the same conditions, two different forms of TNF-β, with molecular weights of about 20,000 (148 residues) and 25,000 (171 residues), have been found[2,3]. The 20 kD species is a proteolytic cleavage product of the 25 kD form.[2,3] The molecular weight of TNFs under non-denaturing conditions are very different. Purified human TNF-α has a native molecular weight of 45,000[8], whereas TNF-β elutes at a position corresponding to a molecular weight of 60–70,000[2,3] during gel filtration. The isoelectric points (pI) of these cyto-toxic factors have been reported to be in the range of 4.5–6.5. TNF-β has a pI of 5.8, and 5.3 is the pI determined for TNF-α.

The amino acid sequence of human TNF-α as determined from the protein[6,7,11] or predicted from the nucleotide sequence[6,7,10,11] has been described. Some variations in the protein sequences at the amino terminal end have been observed. The N-terminal protein sequence of the natural human TNF-α purified from HL-60 cells obtained by Wang et al.,[7] has two discrepancies with the sequence reported earlier[8] and that predicted from the cloned cDNA sequence[5,7]. Two out of the three serines in positions 3–5 of the mature protein are missing, and the His-Val sequence in position 15 and 16 has been replaced by Val-Ser-Val-Ser. The reason for this discrepancy is not clear. Two groups[6,11] have reported the N-terminal sequence of recombinant human TNF-α expressed and purified in *E. coli* in which Val-Arg from position 1 and 2 of the natural protein sequence, respectively, are missing, even though the nucleotide codons for these amino acids are present at the corresponding positions in both the genomic[6] and cDNA[11] sequences. These investigations assumed that the N-terminal sequence of human TNF-α was Ser-Ser-Ser-Arg-. . . based on an analogy with the sequence of rabbit TNF-α purified from serum.

TNF-α has been extensively studied and has been found to exert a variety of effects on normal cells. One major indication of an effect of TNF-α on normal tissue stems from studies on cachectin[12,13,14], a macrophage secreted factor that inhibited the synthesis of lipoprotein lipase in the mouse adipocyte cell line 3T3-L1. Cachectin has been suggested to be the agent responsible for causing cachexia during certain chronic host infections and malignancies.[14,15] One of the salient features of cachexia is the loss of body weight, even with adequate food consumption. The purification of cachectin and its partial structure determination revealed that this protein was identical to TNF-α.[12,13] These studies have prompted the suggestion that TNF-α is the agent responsible for cachexia during chronic host infection.[14,15] However, recent studies indicate that this activity is not unique to TNF-α, since other cytokines including IL-1[16], IFNs[17,18], and TNF-β[18] can also suppress lipoprotein lipase activity in 3T3-L1 adipocytes.

Tumor necrosis serum (TNS) and partially purified preparations of TNF-α have been reported to protect animals against bacterial and parasitic infections. C3H/HeJ mice challenged with *Klebsiella pneumoniae* or *Listeria monocytogenes* showed increased survival rates following TNS injection compared to untreated controls.[19] TNF-α also appears to have a potent cytotoxic effect on the malarial parasites *Plasmodium falciparum*[20], *Plasmodium yoelii* and *Plasmodium berghei*.[21] Recently recombinant TNF-α was shown to be similar to eosinophil cytotoxicity enhancing factor and it potentiated eosinophil cytotoxicity against *Schistosoma mansoni* larvae.[22]

Several investigators have found that rTNF-α exhibits direct antiviral activity similar to interferons. TNF-α protected HEP-2 cells against VSV infection[24] and this effect was not blocked by anti-IFN antibodies.[24] Similarly, TNF-α and TNF-β were shown to directly induce resistance to infection by both RNA viruses (EMCV and VSV) and DNA viruses (Ad-2 and HSV-2) in diverse cell types.[25] The antiviral effect of TNFs was not IFN-mediated since it was not abolished by anti-IFN-α, -β, or -γ antibodies, there were no detectable levels of IFNs in the cell culture fluids, and no IFN mRNA was found in the cells. In addition to inducing the antiviral state, TNFs were also able to selectively kill virus-infected cells. Both the antiviral activity and the virus-induced cytotoxicity of TNFs were synergistically enhanced by IFNs.[25] Furthermore, viruses as well as the polymer poly(I):poly(C) could induce the production of TNF-α in HL-60 cells and TNF-β, in RPMI 1788 cells.[25]

A role for TNF in mediating inflammatory responses has been implicated by its effects on neutrophil functions. It has been reported[26] that pretreatment of PMN with purified TNF-α and TNF-β, (free of detectable LPS contamination) induces a significant increase in their ability to phagocytose fluorescein-conjugated latex beads as well as an enhancement of PMN-mediated antibody dependent cellular cytotoxicity (ADCC) against chicken erythrocytes. More recently other investigators[27] have found significant increases in phagocytosis of unopsonized zymosan particles, degranulation, and respiratory burst activity by TNF-α treated PMN. Interestingly, these effects were inhibited by monoclonal antibodies against the C3bi receptor/adherence glycoprotein CD11.[28] TNF-α has been shown[29] to increase the expression of this protein on neutrophils resulting in their enhanced adherence to the endothelium.

In addition to its effects on PMN, TNF-α appears to have direct effects on endothelial cells which play a major role in inflammation and tissue injury. TNF-α induced the release of IL-1 from endothelial cells[30] and induces neutrophil adherence to endothelial cells[29,31] via the CDW18 neutrophil membrane protein complex (also called the C3bi receptor/adherence glycoprotein mentioned earlier). Further evidence that the endothelium is a major site of TNF action in vivo comes from studies on effects of TNF-α on the hemostatic properties of endothelial cells[33] in culture. Incubation with rTNF-α causes changes in the production of two activities:[33] induction of tissue factor, a procoagulant cofactor protein[34,35], and inhibition of formation of activated protein C, an anticoagulant cofactor protein[36]. Extensive changes in the morphology of human vascular endothelial cells in confluent primary culture treated with TNF-α have also been reported[37].

A possible role for TNF-α and TNF-β, in granulocyte-macrophage differentiation has been suggested from recent observations by two groups of investigators who have found that TNF-α[41] and TNF-β[42] suppress colony formation by bone-marrow derived hematopoietic progenitor cells. Low doses (0.05–100 U/ml) of rTNF-α[41] as well as TNF-(Luk II)[43] inhibited granulocyte-macrophage differentiation by both late (CFU-GM, day 7) and early (DFU-GM, day 14) precursor cells. The effect was rapid, since pulsing the bone marrow cells for only one hour with TNF-α was sufficient to cause suppression. Inhibition of colony formation by erythroid (BFU-E) as well as multi-potential (CFU-GEMM) progenitor cells was also observed[41]. All of these effects could be seen in non-adherent bone marrow cells substantially depleted (down to 2 percent) of monocytes and T lymphocytes[41]. The inhibitory effect of TNF-β on CFU-GM was observed in the presence of IFN-γ[42].

A number of intracellular activities have been reported. They include stimulation of IL-1 and $PGE_2$ production in resting macrophages[44], induction of class I (but not the immunologically more significant class II antigens) protein antigens of the major histocompatibility complex[32], induction of synthesis of collagenase and $PGE_2$ in synovial cells and dermal fibroblasts[45], fragmentation of target-cell DNA into discretely sized pieces[46], induction of GM-CSF in normal human lung fibroblasts[48], stimulation of complement component C3 in human hepatoma cells[49], and depression of cytochrome P450 and drug metabolizing enzymes (ethoxycoumarin deethylase and arylhydrocarbon hydroxylase) in mouse liver[50].

The true physiologic role of TNFs in vivo requires knowledge of their relationship to other monokines and lymphokines. In recent years it has become increasingly evident that cytokines acting locally, such as interleukins, interferons, etc., play an important and interdependent role in modifying biological responses. In the immune response, these mediators produce autocrine as well as paracrine effects during T and B cell activation[51]. For instance, macrophages secrete IL-1, which induces T cells to secrete IL-2 and this in turn causes secretion of IFN-γ, which can cause the production of TNF-α and TNF-β. Human peripheral blood mononuclear cells (PBMC) were shown to be induced by rIL-2 to secrete both TNF-β[52,53] and TNF-α[53], and the effect of IL-2 was augmented by rIFN-γ[52,53]. In some instances IFN-γ by itself also induced TNF-α/TNFβ production[54]. TNF-α production could be seen within 3 hours after induction, reaching peak levels at 48 hr and declining thereafter; TNF-β production started at a slower rate, requiring greater than 8 hours and reached a peak in 72 hr; IFN-γ did not alter the kinetics of TNF-α/TNF-β induction by IL-2[56]. Conversely, TNF itself was reported to have stimulated lymphocytes to secrete IFN-γ[54], FS-4 fibroblasts to synthesize IFN-$β_2$[23], and endothelial cells[30], monocytes[55,56], and macrophages[44] to release Il-1.

Besides regulation of TNF-α/TNFβ production by other cytokines, in order to fully comprehend the true physiological role of TNFs, one must also consider their relationship to the monokine IL-1 and the lymphokine, IFN-γ. There are many simiilarities between the biological action of TNFs and IL-1, and the presence of IFN-γ together with TNFs, results in markedly synergistic or antagonistic responses. These actions are briefly described below.

TNFs share a number of biological activities with IL-1, another distinct 17,000 Da protein produced by monocytes, which plays a major role in mediating the immune response[58]. Some common biological activities of these two monokines include: endogenous pyrogenic activity in vivo[56], induction of procoagulant activity in endothelial cells[33,38], stimulation of bone resorption and cartilage resorption, stimulation of collagenase and $PGE_2$ production in dermal fibroblasts[45,57], suppression of lipoprotein lipase activity in adipocytes, stimulation of growth of fibroblasts[58], cytocidal activity against several neoplastic cell lines and anti-tumor activity in vivo. However, differences in biological activity between TNFs and IL-1 also exist, for example, TNF has a rapid direct cytostatic and cytotoxic activity against a wide variety of neoplastic tissues, whereas the cytostatic properties of IL-1 requires coincubation for at least 48 hours and has been observed only against a single human melanoma cell line (A-375). IL-1 also has in vitro adjuvant activity for increasing specific cytotoxic T lymphocytes following coculture of "naive" lymphocytes with allogeneic stimulator cells, an in vitro property not shared with TNF. IL-1 does not activate PMN[67]. IL-1 does not inhibit stem cell colony formation[68].

Several investigators have found that the in vitro tumoricidal activity of TNFs is significantly augmented by co-incubation with IFNs. IFN-α, -β or -γ, while not showing any antiproliferative effects by themselves, synergistically enhanced the cytotoxicity of TNF-α/TNF-β. Synergism between IFN-γ and TNF-β has also been reported[42] for inhibition of hematopoietic cell differentiation. Furthermore, the synergistic effect of IFN-γ appears to be correlated with its ability to induce synthesis of TNF receptors in target cells. It is unclear whether the synergism is solely explained by increased receptor number, or whether other proteins involved in the mechanism of cytotoxicity are also induced by IFN-γ.

It is clear from the foregoing discussion that expectations of the in vivo mechanism of action of TNFs are complicated by virtue of their diverse biological effects, their interaction with other monokines and lymphokines, and the target tissues or cells involved.

SUMMARY OF THE INVENTION

The objects of this invention are accomplished by a method which comprises administering to an animal (a) a substance against which it is desired to raise an immune response and (b) an adjuvant effective amount of tumor necrosis factor-α or tumor necrosis factor-β.

DETAILED DESCRIPTION OF THE INVENTION

The animals to be treated in accordance with this invention are those which are capable of mounting an immune response to an antigen. This includes mammals, particularly man, but also commercial livestock such as beef, swine, sheep, chickens and the like.

The substance against which it is desired to raise an immune response is referred to herein as the antigen, but it will be appreciated that in many circumstances the substance is not immunogenic in the subject animal without the intervention of an adjuvant and in fact may be entirely homologous to the animal. A substance is not normally antigenic where the subject to be immunized has no detectable titer of antibody or cytotoxic T lymphocyte (CTL activity) against the substance prior to immunization, or it has been unable to mount a cytotoxic or neutralizing immune response (cellular or humoral) against the substance. This is the case with many tumor antigens, for example, and in circumstances where it is desired to create an autoimmune response to modulate growth or reproductive functions. Typical antigens are those found on autochthonous syngeneic tumor cells which have been removed from the subject, or somatostatin fusions with immunogenic polypeptides for increasing growth in agricultural animals. Other antigens for use herein are viral polypeptides, hormones including polypeptide reproductive hormones such as LHRH, inhibin or the prosequence of the alpha chain of inhibin, growth factors such as TGF-β or TGF-α, somatostatin, cell surface receptors for growth hormones, and synthetic low molecular weight polypeptides (e.g., about from 3 to 15 residues).

The immune response to the antigen is enhanced by conjugating the antigen to a polypeptide which is immunogenic in the animal to be immunized, e.g. BSA, KLH, soybean trypsin inhibitor, or microbial or viral proteins such as beta-lactamase, the herpes gD protein, or fragments thereof. Conjugation is conventional and typically includes covalent fusion of the antigen to the immunogenic polypeptide by in vitro chemical techniques or by expression in recombinant cell culture from a gene in which DNA encoding the immunogenic polypeptide is ligated in frame to DNA encoding the antigen. Haptenic, nonpolypeptide antigens in particular are conjugated by in vitro crosslinking to immunogenic proteins such as KLH or BSA in accord with known practice.

The antigen or its immunogenic conjugate optionally is noncovalently adsorbed to or deposited on carriers known per se, e.g., alum or liposomes.

TNF-α and TNFγ are obtained from recombinant or nonrecombinant sources, although the former is preferred for reasons of economy. Included within the scope of TNF-α and TNF-γ are glycosylated and unglycosylated forms, amino acid sequence variants wherein one or more amino acid residues have been inserted, deleted or substituted, and covalent derivatives obtained by in vitro chemical modification, so long as they exhibit the same qualitative effect on the immune system as the parental molecule. Preferably the TNF-α to be selected is the ValArg N-terminal species synthesized in recombinant bacterial cell culture as described in U.S. Ser. No. 677,156 and the TNF-β is the His-23 N-terminal unglycosylated species described in U.S. Ser. No. 732,312. Preferably, the vaccination will use TNF-α as adjuvant, although TNF-β is used together with TNF-α or in sequence with TNF-α in booster vaccinations. The TNF and antigen optionally are administered together with adjuvant effective amounts of other lymphokine or monokine adjuvants such as IL-1 and/or γ-interferon. While the TNFs are not known to be species specific, it is preferable to use TNFs that are homologous to the species to be immunized.

The adjuvant effective amount of TNF-α and TNF-β used in the method of this invention will be determined by the clinician taking into account the method and site of delivery of the adjuvant, the method and site of delivery of the TNF-α and/or TNF-β, whether the TNF is administered together with γ-interferon or IL-1, the inherent immunogenicity of the antigen, the desired form of the response (elevation of titer, prolongation of the response, or both), the presence of carriers and other considerations that will be apparent to those skilled in the art. Typically, the amount of TNF-α or TNF-β will range about from 10 to 500 micrograms of TNF per Kg of body weight per dose, with daily doses for about 1 to 7 days, and optionally up to 13 days, for a period sufficient to elicit the desired response—generally 1 to 4 weeks. Both IFN-γ and a TNF optionally are included in the dose. Similarly, the presence of a carrier such as alum in the dosage form also will reduce the amount of TNF required. Preferably the TNF is continuously administered at the lower end of the range described above (about from 10 to 75 micrograms/Kg) by an in situ deposition at the vaccination site. This is accomplished, for example, by embedding the TNF in a sustained release composition such as a liposome or a permeable/biodegradable polymer matrix, e.g. polylactide, and inserting or injecting the composition at the vaccination site. The antigen also can be incorporated into the composition.

Doses of antigen will vary widely, and must be determined empirically. Where autochthonous tumor cells are serving as the target, generally about from $1 \times 10^6$ to $50 \times 10^6$ cells are administered per Kg of body weight per dose. Each dose preferably is administered at a plurality of sites, and preferably by intradermal or intramuscular injection. Generally the antigen will be administered together with adjuvant although boosters with antigen may not require adjuvant. However, one must use a dose of TNF which is less than the maximum tolerated dose (MTD). This will vary among animal species and will also depend upon the TNF used, the rate of administration and the route of administration.

In humans, the i.m. MTD for TNF-α is about from 20 to 40 micrograms/m². It is not undesirable that the TNF-α induce minor localized induration and erythema, but doses producing subdural necrosis are to be avoided. It should be appreciated that the optimal adjuvant dose generally will be considerably less than the MTD, but this must be determined empirically.

The adequacy of the vaccination parameters chosen, e.g. dose, schedule, adjuvant choice and the like, is determined by taking aliquots of serum from the subject animal and assaying antibody titers during the course of the immunization program. Alternatively, the presence of immune T cells can be monitored. In addition, the clinical condition of the animal will be monitored for the desired effect, e.g. antitumor activity or growth modulation. If inadequate vaccination is achieved then the animal can be boosted with further antigen vaccinations and the vaccination parameters can be modified in a fashion expected to potentiate the immune response, e.g. increase the amount of antigen and/or adjuvant, complex the antigen with a carrier or conjugate it to an immunogenic protein, or administer the antigen intraperitoneally.

The invention will be more fully understood in the light of the following examples. All literature and patent document citations are expressly incorporated by reference.

EXAMPLE 1

The objective of this example is to demonstrate the adjuvant effect of TNF, and TNF together with IFN-γ, in immunizing an animal against a challenge by syngeneic or allogeneic tumor cells.

C3H/HeN mice were immunized with $1 \times 10^5$ radiation killed 2237 tumor cells. The 2237 cell line is a moderately antigenic syngeneic fibrosarcoma obtained from s.c. growing tumors by collagenase dissociation. The donor tumor cells for use in tumor vaccine were irradiated with 10,000 R of gamma irradiation. Irradiation ultimately kills the cells but they are not immediately killed, indeed the cells may be able to undergo one or two additional divisions before a sufficient accumulation of chromosomal breaks or other abnormalities is obtained to result in a lethal event. Thus, irradiation results in a metabolically viable but noncontinuously proliferating cell. The cells were admixed with HBSS alone (serving as a non-adjuvant killed cell control vaccine), or with HBSS containing various doses of homogeneous recombinant Val-terminal human TNF-α alone or TNF-α plus IFN-γ. The mixture was injected intradermally into the posterior ventral region at five sites. Controls also included TNF without tumor cells, injections of HBSS alone (without killed 2237 cells), and FK565, a dimuramyl dipeptide derivative representing a known adjuvant as a positive control. Primary immunization with 2237 cells and TNF-α occurred on day 1; TNF-α was administered intraperitoneally alone on days 2 and 3. Secondary intradermal immunization occurred on day 11 with the same number of killed cells. When IFN-γ was used with TNF-α, IFN-γ administrations accompanied the TNF-α administration and further, IFN-γ, TNF-α or IFN-γ plus TNF-α were administered intraperitoneally on days 12 and 13. Five days after the second immunization the animals' footpads were injected with live 2237 cells. 48, 74 and 81 days later the tumors that had developed were measured by calipers in two dimensions. Numerous control animals had died by the last measurement day. The Table below depicts the results of this study, demonstrating adjuvant activity on the part of TNF-α or TNF-α and IFN-γ. Tumor volume was determined using the formula for a prolated sphere using the two dimensions previously measured. The formula is tumor volume (cm³) equals ½ A×B²; where A equals the larger tumor diameter and B equals the smaller tumor diameter.

TABLE

| | | Tumor Volume (cm³) | | |
|---|---|---|---|---|
| Group | Dose Per Animal | Day 48 | Day 74 | Day 81 |
| 1. HBSS | 0 | 0.540 | 1.608 | 4.33 |
| 2. Vaccine only | $1 \times 10^5$ cells | 0.024 | 1.6511 | 1.12 |

TABLE-continued

| Group | Dose Per Animal | Tumor Volume (cm³) | | |
|---|---|---|---|---|
| | | Day 48 | Day 74 | Day 81 |
| 3. FK565 | 500 µg | 0 | 0 | 0 |
| 4. TNF-α | 5 µg | 0 | 0 | 0 |
| 5. TNF-α | 1 µg | 0.157* | 0 | 0 |
| 6. TNF-α | 0.1 µg | 0 | 0 | 0 |
| 7. TNF-α/IFN-γ | 5 µg/5 × 10⁴ units | 0 | 0 | 0 |
| 8. TNF-α/IFN-γ | 1 µg/5 × 10⁴ units | 0 | 0 | 0 |
| 9. TNF-α/IFN-γ | 0.1 µg/5 × 10⁴ units | 0 | 0 | 0 |
| 10. IFN-γ | 5 × 10⁴ units | 0 | 0 | 0 |

*The tumor that had developed in one animal in this group regressed before the end of the study.

These results clearly demonstrate the immunoprotective adjuvant activity of TNF alone or together with IFN-γ. The effective molar dosage of TNF was only 1/1,000 of that needed to achieve protection using a conventional adjuvant (FK565).

Neither TNF-α nor IFN-γ have any significant direct cytotoxic effect on 2237 cells. This is not especially relevant in the context of the foregoing experiments because the tumor cells were not injected into the animals until 2 days after they had last been exposed to cytokines.

Murine TNF-α produced substantially the same result as human TNF-α in a replicate of this study.

TNF-α also was able to stimulate the development of cytotoxic T cells in 2237-cell immunized mice, thus confirming that the in vivo results were consistent with the conclusion that TNF was acting as an adjuvant boosting cell-mediated immunity in the immunized animals.

The preceding example was based on the induction of cytotoxic T lymphocytes, which are required to reject a syngeneic tumor challenge. In addition to the adjuvant activity of TNF-α alone or in combination with IFN-γ for syngeneic tumor vaccines, TNF-α can also act as an adjuvant for inducing serum antibodies to soluble antigen BSA.

EXAMPLE 2

The purpose of this example was to demonstrate the adjuvant affect of TNF in inducing serum antibodies to a specific foreign protein (BSA) as a model antigen.

C3H/HeN mice were given an i.p. injection of bovine serum albumin using a suboptimal vaccine dose (500 µg/animal), which was administered by i.p. injection on day 0. Various doses of TNF-α, as an adjuvant, were administered 48 hours following a second injection of BSA at 100 µg/animal. The mice were bled three days later and the serum antibody levels as IgG were determined using routine Elisa techniques. The i.v. injection of maleic divinyl ether with an average molecular weight of 20,000 daltons was used as a positive control. Both MVE-2 or rH TNF-α in a dose-dependent manner augmented the production of antibody (IgG) against BSA. As additional controls, the injection of TNF alone did not induce serum antibody activity.

These results clearly demonstrate the adjuvant activity of TNF-α for the induction of high serum antibody titers directed against soluble antigens. Thus,TNF-α has adjuvant activity for a wide variety of proteinaceous antigens such as hormones or infectious agents including viruses and cellular microbes.

BIBLIOGRAPHY
1. Talmadge, J. E. et al., "Behring Inst. Mitt." 74:189 (1984).
2. Aggarwal, B. B., Moffat, B., and Harkins, R. N., Human Lymphotoxin, "J. Biol. Chem." 259:686 (1984).
3. Aggarwal, B. B., Henzel, W. J., Moffat, B., Kohr, W. J., and Harkins, R. N., Primary Structure of Human Lymphotoxin Derived from 1788 Lymphoblastoid Cell Line, "J. Biol. Chem." 260:2334 (1985).
4. Gray, P. W., Aggarwal, B. B., Benton, C. V., Bringman, T. S., Henzel, W. J., Jarrett, J. A., Leung, D. W., Moffat, B., Ng, P., Svedersky, L. P., Palladino, M. A., and Nedwin, G. E., Cloning and Expression of CDNA for Human Lymphotoxin, a Lymphokine with Tumor Necrosis Activity, "Nature" 312: 721 (1984).
5. Pennica, D., Nedwin, G. E., Hayflick, J. S., Seeburg, P. H., Derynck, R., Palladino, M. A., Kohr, W. J., Aggarwal, B. B., and Goeddel, D. V., Human Tumour Necrosis Factor: Precursor Structure, Expression, and Homology to Lymphotoxin, "Nature" 312:724 (1984).
6. Shirai, T., Yamaguchi, H., Ito, H., Todd, C. S. and Wallace, R. B., Cloning and Expression in *Escherichia coli* of the Gene for Human Tumour Necrosis Factor, "Nature" 313:803 (1985).
7. Wang, A. M., Creaseyi A. A., Ladner, M. B., Lin, L. S., Strickler, J., Van Arsdell, J. N., Yamamoto, R. and Mark D.F., Molecular Cloning of the Complementary DNA for Human Tumor Necrosis Factor, "Science" 228: 149 (1985).
8. Aggarwal, B. B., Kohr, W. J., Hass, P. E., Moffat, B., Spencer, S. A., Henzel, W. J., Bringman, T. S., Nedwin, G. E., Goeddel, D. V., and Harkins, R. N., Human Tumor Necrosis Factor: Production, Purification and Characterization, "J. Biol. Chem. 260:2345 (1985).
9. Nakamura, M. et "Nature" 307:381 (1984).
10. Marmenoit, A., Fransen, L., Tavernier, J., Van der Heyden, U., Tizard, R., Kawashima, E., Shaw, A., Johnson, M. -J., Semon, D., Muller, R., Ruysschaert, M. -R., Van Vliet, A., and Fiers, W., Molecular Cloning and Expression of HumanTumor Necrosis Factor and Comparison with Mouse Tumor Necrosis Factor "Eur. J. Biochem." 152: 515 (1985).
11. Yamada, Y., Furutani, Y., Notake, M., Yamagishi, J., Yamayoshi, M., Fukui, T., Nomura, H., Komiya, M., Kuwashima, J., Nakano, K., Sohmura, Y., and Nakamura, S., Efficient Production of Human Tumour Necrosis Factor in Eschericia coli, "J. of Biotechnology" 3: 141 (1985).
12. Buetler, B. A., Milsark, I. W., and Cerami, A., Cachectin/Tumor Necrosis Factor: Production, Distribution and Metabolic Fate In Vivo, "J. Immunol." 135: 3972 (1985).
13. Buetler, B., Greenwald, D., Hulmes, J. D., Chang, M., Pan, Y. C., Mathison, J., Ulevitch, R., and Cerami, A., Identity of Tumour Necrosis Factor and the Macrophage-Secreted Factor Cachectin, "Nature" 316: 552 (1985).
14. Torti,F. M., Dieckmann,B., Buetler,B., Cerami,A., and Ringold, G. M., A Macrophage Factor Inhibits Adipocyte Gene Expression: An In Vitro Model of Cachexia, "Science" 229:867 (1985).
15. Beutler,B., Milsark,I. W., and Cerami,A. C., Passive Innunization Against Cachectin/Tumor Necrosis Factor Protects Mice from Lethal Effect of Endotoxin, "Science" 229:869 (1985).
16. Buetler, B. A. and Cerami, A., Recombinant Interleukin 1 Suppresses Lipoprotein Lipase Activity in 3T3 L1 Cells, "J. Immunol." 135: 3969 (1985).
17. Keay, S. and Grossberg, S. E., Interferon, Inhibits the Conversion of 3T3 L1 Fibroblasts into Adipocytes, "Proc. Natl. Acad. Sci. USA" 77: 4099 (1980).
18. Patton, J. S., Shepard, H. M., Wilking, H., Lewis, G., Aggarwal, B. B., Eessalu, T. E., Gavin, L. A., and Grunfeld, C., Interferons and Tumor Necrosis Factors Have Similar Catabolic Effects on 3T3 L1 Cells, "Proc. Natl. Acad. Sci., in press.
19. Parent, M., Antimicrobial Resistance Enhancing Activity of Tumor Necrosis Serum Factor Induced by Endotoxin in BCG-Treated Mice, "Recent Results Cancer Res." 75:213 (1980).
20. Hardaris, C. G., Haynes, J. D., Meltzer, M. S. and Allison, A. C., Serum Containing Tumor Necrosis Factor is Cytotoxic for the Human Malaria Parasite *Plasmodium falciparum*, "Infect. and Immun." 42: 385 (1983).
21. Taverne, J., Matthews, N., Depledge, P., and Playfair, J. H. L., Malarial Parasites and Tumor Cells are Killed by the Same Component of Tumor Necrosis Serum, "Clin. Exp. Immunol." 57: 293 (1984).
22. Silberstein, D. and David, J. R., Tumor Necrosis Factor Enhances Eosinophil Toxicity to *Schistosoma mansoni* Larvae, "Proc. Natl. Adac. Sci." 83: 1055 (1986).
23. Kohase, M., Henricksen-DeStefano, D., May, L. T., Vilcek, J. and Sehgal, P. B., Induction of $\beta_2$-Interferon by Tumor Necrosis Factor: A Homeostatic Mechanism in the Control of Cell Proliferation, "Cell" 45: (1986).
24. Mestan, J., Digel, W., Jacobsen,. H., Hillen, H., Blohm, D., Moller, A., and Kirchner, H., In Vitro Antiviral Effects of Recombinant Tumor Necrosis Factor, "Nature" 323: 816 (1986).
25. Wong, G. C. and Goeddel, D. V., Tumour Necrosis Factors-$\alpha$ and -$\beta$ Inhibit DNA and RNA Virus Replication and Synergize with Interferons, "Nature" 323: 819 (1986).
26. Shalaby, M. R., Aggarwal, B. B., Rinderknecht, E., Svedersky, L. P., Finkle, B. S., and Palladino, M. A. Jr., Activation of Human Polymorphonuclear Neutrophil Functions by Interferon-Gamma and Tumor Necrosis Factor, "J. Immunol." 135: 2069 (1985).
27. Klebanoff, S. J., Vadas, M. A., Harlan, J. M., Sparks, L. H., Gamble,. J. R., Agosti, J. M. and Waltersdorph, A. M., Stimulation of Neutrophils by Tumor Necrosis Factor, "J. Immunol." 136:4220 (1986).
28. Harlan, J. M., Killei, P. D., Senecal, F. M., Schwartz, S. R., Yee, E. K., Taylor, R. F., Beatty, P. G., Price, T. H. and Ochs, H. D., The Role of Neutrophil Membrane Glycoprotein GP 150 in Neutrophil Adherence to Endothelium In Vitro, "Blood" 66:167 (1985).
29. Gamble, J. R., Harlan, J. M., Klebanoff, S. J., and.Vadas, M. A., Stimulation of the Adherence of Neutrophils to Umbilical Vein Endothelium by Human Recombinant Tumor Necrosis Factor, "Proc. Natl. Acad. Sci. USA" 82:8667 (1985).
30. Nawroth, P. O., Bank, I.,Handley, D., Cassimeris, J., Chess, L., and Stern, D., Tumor Necrosis Factor/Cachectin Interacts with Endothelial Cell Receptors to Induce Release of Interleukin-1, "J. Exp. Med." 163:1363 (1986).
31. Pohlman, T. H., Stanness, K. A., Beatty, P. G., Ochs, H. D., and Harlan, J. M., An Endothelial Cell Surface Factor (s) Induced In Vitro by Lipopolysaccharide, Interleukin 1, and Tumor Necrosis Factor-$\alpha$ Increases Neutrophil Adherence by a CDW18-Dependent Mechanism, "J. Immunol." 136:4548 (1986).
32. Collins, T., Lapierrei L. A., Fiers, W., Strominger, J. L., and Pober, J. S., Recombinant Human Tumor Necrosis Factor Increases mRNA Levels and Surface Expression of HLA-A,B Antigens in Vascular Endothelial Cells and Dermal Fibroblasts In Vitro, "Proc. Natl. Acad. Sci. USA" 83:446 (1985).
33. Nawroth, P. O. and Stern, D. M., Modulation of Endothelial Cell Hemostatic Properties by Tumor Necrosis Factor, "J. Exp. Med." 164: 740 (1986).
34. Bach, R., Nemerson, Y., and Konigsberg, W., Purification and Characterization of Bovine Tissue Factor, "J. Biol. Chem." 256:8324 (1981).
35. Stern, D. M., Nawroth, P., Handley, D., and Kisiel, W., An Endothelial Cell Dependent Pathway of Coagulation, "Proc. Natl. Acad. Sci. USA" 82: 2523 (1985).
36. Esmon, N., Owen, W., and Esmon, C., Isolation of a Membrane-Bound Cofactor for Thrombin-Catalyzed Activation of Protein C, "J. Biol. Chem." 257: 859 (1982).
37. Stolpen, A. H., Guinan, E. D., Fiers, W., and Pober, J. S., Recombinant Tumor Necrosis Factor and Immune Interferon Act Singly and in Combination to Reorganize Human Vascular Endothelial Cell Monolayers, "Am. J. Pathol." 23:16 (1986).
38. Stern, D. M., Bank, I., Nawroth, P. P., Cassimeris, J., Kisiel, W., Fenton, J. W., Dinarello, C., Chess, L., and Jaffe, E. A., Self-Regulation of Procoagulant Events on the Endothelial Cell Surface, "J. Exp. Med." 16:1223 (1985).
39. Yamada, M., Yamayoshi, M., Furuta, R., Kotani, H., Asaka, Y., Nakata, K., Yoshida, H., Kashimoto, S., and Nakamura, S., Biochemical and Biological Properties of Recombinant Human Interleukin-1 Alpha, *Sixth International Congress of Immunology* Abstract No. 3.31.7, p. 344, (1986).
40. Hirai, Y., Nakai, S., Nishino, N., Nishida, T., Yanagihara, Y., and Kikumoto., Y., Anti-Tumor Effect of Recombinant Human GIF-$\alpha$/IL-1$\beta$, *Sixth International Congress of Immunology*, Abstract No. 3.31.40, P. 349 (1986).
41. Degliatoni, G., Murphy, M., Kobayashi, M., Francis, M. K., Perussia, B., and Trinchieri, G., Natural Killer (NK) Cell-Derived Hematopoietic Colony-Inhibiting Activity and NK Cytotoxic Factor. Relationship with Tumor Necrosis Factor and Synergism with Immune Interferon, "J. Exp. Med." 16: 1512 (1985).
42. Murphy, M., Loudon, R., Kobayashi, M., and Trinchieri, G., $\gamma$-Interferon and Lymphotoxin,. Released by Activated T Cells, Synergize to Inhibit Granulocyte/Monocyte Colony Formation, "J. Exp. Med." 164:263 (1986).
43. Broxmeyer, H. E., Williams, D. E., Lu, L., Cooper, S., Anderson, S. L., Beyer, G. S., Hoffman, R., Rubin, B. Y., The Suppressive Influence of Human Tumor Necrosis Factors on Bone Marrow Hematopoietic Progenitor Cells from Normal Donors and Patients with Leukemia: Synergism of Tumor Necrosis Factor and Interferon-Gamma, "J. Immunol." 136:448 (1986).
44. Bashwich, P. R., Chensue, S. W., Larrick, J. W. and Kunkel, S. W., Tumor Necrosis Factor Stimulates Interleukin-1 and Prostaglandin $E_2$ Production in Resting Macrophages, "Biochem. Biophys. Res. Commun." 16:94 (1986).
45. Dayer, J.- M., Beutler, B., and Cerami, A., Cachectom/Tumor Necrosis Factor Stimulates Synovial Cells and Fibroblasts to Produce Collagenase and Prostaglandin $E_2$, "J. Exp. Med." 162: 2163 (1985).
46. Schmid, D. S., Tite, J. P., and Ruddle, N. H., DNA Fragmentation: Manifestation of Target Cell Destruction Mediated by Cytotoxic T-Cell Lines, Lymphotoxin-Secreting Helper T-Cell Clones, and Cell-Free Lymphotoxin-Containing Supernatant, "Proc. Natl. Acad. Sci.USA" 83:1881–1885 (1986).
47. M. Staruch et al. "J. Immunol." 130:2191 (1983).
48. Munker, R., Gasson, J., Ogawa, M., Koeffler, H. P., Recombinant Human TNF Induces Production of Granulocyte-Monocyte Colony-Stimulating Factor, "Nature" 323: 79 (1986).
49. Darlington, G. J., Wilson, D. R., Lachman, L. B., Monocyte-Conditioned Medium, Interleukin-1, and Tumor Necrosis Factor Stimulate the Acute Phase Response in Human Hepatoma Cells In Vitro, "J. Cell. Biol." 103: 787 (1986).
50. Ghezzi, P., Saccardo, B., and Bianchi, M., Recombinant Tumor Necrosis Factor Depresses Cytochrome P450-Dependent Microsomal Drug Metabolism in Mice, "Biochem. Biophys. Res. Commun." 136: 316 (1986).
51. Friedman, R. M., and Vogel, S. N., Interferons with Special Emphasis on the Immune System, "Adv. Immunol." 34: 97 (1983).
52. Svedersky, L. P., Nedwin, G. E., Goeddel, D. V. and Palladino, M. A., Interferon-γ Enhances Induction of Lymphotoxin in Recombinant Interleukin-2 Stimulated Peripheral Blood Mononuclear Cells, "J. Immunol." 134: 1604 (1985).
53. Nedwin, G. E., Svedersky, L. P., Bringman, T. S., Palladino, M. A. Jr., and Goeddel, D. F., Effect of Interleukin-2, Interferon-Gamma, and Mitogens on the Production of Tumor Necrosis Factors Alpha and Beta, "J. Immunol." 135: 2492 (1985).
54. Wong, G. H. W. and Goeddel, D. V., Interferon-7 Induces the Expression of Tumor Necrosis Factor/Lymphotoxin and Vice Versa, *Sixth International Congress of Immunolog*, Abstract No. 3.33.43, p. 365 (1986).
55. Phillip, R., and Epstein, L. B., Tumour Necrosis Factor as Immunomodulator and Mediator of Monocyte Cytotoxicity Induced by Itself, γ-Interferon and Interleukin-1, "Nature" 2: 86 (1986).
56. Dinarello, C. A., Cannon, J. G., Wolff, S. M., Bernheim, H. A., Beutler, B., Cerami, A., Figari, I. S., Palladino, M. A. Jr., and O'Connor, J. V., Tumor Necrosis Factor (Cachectin) is an Endogenous Pyrogen and Induces Production of Interleukin-1, "J. Exp. Med." 163: 1433 (1986).
57. Pujol, J. P., Penfornis, H., Arenzana-Seisdedos, F., Bocquet, J., Farjanel, J., Rattner, A., Brisset, M., Virelizier, J. L., Beliard, R. and Loyau, G., Mononuclear Cell-Mediated Modulation of Synovial Cell Metabolism. I. Collagen Synthesis, "Exp. Cell. Res." 18: 63 (1985).
58. Matsushima, K., Durum, S. K., Kimball, E. S., and Oppenheim, J. J., Purification of Human Interleukin-1 and Identity of Thymocyte Co-mitogenic Factor, Fibroblast Proliferation, Acute Phase Inducing Factor and Endogenous Pyrogen, "Cell. Immunol." 29: 290 (1985).
59. J. Freund, "Adv. Tuberc. Res." 7:130 [1956].
60. R. White "Ann. Rev. Microbiol." 30:579 [1976].
61. F. Frost et al. "Immunology" 35:63 [1978].
62. A. Allison et al. "Reticuloendothel. Soc." 26[Suppl]:619 [1979].
63. B. Waksman "Springer Sem. Immunopatho." 2:5 [1979].
64. R. Edelman "Rev. Infect. Dis." 2:370 [1980].
65. R. Nervig et al. *Advances in Carriers and Adjuvants for Veterinary Biologics* 11–24 [1986].
66. J. Oppenheim et al. "Cell. Immunol." 50:71 (1980).
67. Bevilacqua, M. P., et al. "J. Clin. Invest. 76:2003–2011 (November 1985).
68. Zucali, J. R. et al. "Blood" 69:33–37 (January 1987).

We claim:

1. A method for enhancing a humoral or cellular immune response in an animal comprising administering to the animal
    (a) a non-tumor substance against which it is desired to raise the immune response; and
    (b) an adjuvant effective amount of tumor necrosis factor (TNF)-alpha, wherein the substance and the TNF-alpha are administered simultaneously and the substance is administered in the form of a conjugate with a microbial or viral polypeptide.

2. A method for enhancing a humoral or cellular immune response in an animal comprising administering to the animal
    (a) a non-tumor substance against which it is desired to raise the immune response; and
    (b) an adjuvant effective amount of tumor necrosis factor (TNF)-alpha, wherein the substance is native to the animal and the substance is a covalent conjugate of somatostatin with a microbial polypeptide.

3. A method for enhancing a humoral or cellular immune response in an animal comprising administering to the animal
    (a) a non-tumor, hapten substance against which it is desired to raise the immune response; and
    (b) an adjuvant effective amount of tumor necrosis factor (TNF)-alpha.

4. A method for enhancing a humoral or cellular immune response in an animal comprising administering to the animal
    (a) an animal virus antigen against which it is desired to raise the immune response; and
    (b) an adjuvant effective amount of tumor necrosis factor (TNF)-alpha.

* * * * *